United States Patent [19]

Nozaki et al.

[11] 4,118,974

[45] Oct. 10, 1978

[54] METHOD AND APPARATUS FOR MEASURING ERYTHROCYTE SEDIMENTATION RATE

[75] Inventors: Hiromi Nozaki; Haruo Hara, both of Hachiohzi, Japan

[73] Assignee: Konishiroku Photo Industry Co., Ltd., Tokyo, Japan

[21] Appl. No.: 766,248

[22] Filed: Feb. 7, 1977

[30] Foreign Application Priority Data

Feb. 17, 1976 [JP] Japan ................................ 51/16626

[51] Int. Cl.² ...................... G01N 15/04; G01N 33/16
[52] U.S. Cl. ........................................ 73/61.4; 356/39
[58] Field of Search ........................ 73/61.4; 356/39; 346/33 A, 33 ME; 340/187; 250/202, 564

[56] References Cited

U.S. PATENT DOCUMENTS

| | | | |
|---|---|---|---|
| 2,419,487 | 4/1947 | Dresser | 340/187 |
| 3,715,761 | 2/1973 | Drekter et al. | 356/39 X |

FOREIGN PATENT DOCUMENTS

| | | | |
|---|---|---|---|
| 2,353,272 | 5/1975 | Fed. Rep. of Germany | 356/39 |
| 2,418,065 | 10/1975 | Fed. Rep. of Germany | 356/39 |
| 1,138,862 | 2/1957 | France | 356/39 |
| 7,424,296 | 2/1976 | France | 356/39 |

*Primary Examiner*—Richard C. Queisser
*Assistant Examiner*—Joseph W. Roskos
*Attorney, Agent, or Firm*—Martin A. Farber

[57] ABSTRACT

In a method of measuring erythrocyte sedimentation rate of the type wherein the upper level of a blood sample contained in a vertical test tube is detected by a photoelectric detection unit, the red blood corpuscles are caused to precipitate for a definite interval and the upper level of the precipitated red blood corpuscles is detected by descending the photoelectric detection unit along the test tube thereby detecting the rate of the sedimentation of red blood corpuscles, the photoelectric detection unit is stopped at a position a small distance corresponding to the air bubble or coagulated substance from the upper level. The photoelectric detection unit is descended after said definite interval for detecting the interface between the blood serum and the precipitated red blood corpuscles. The rate of the sedimentation of the red blood corpuscles is determined in terms of the difference between the position at which the photosensitive detection unit has stopped and the position thereof a predetermined time after detection of the interface.

6 Claims, 7 Drawing Figures

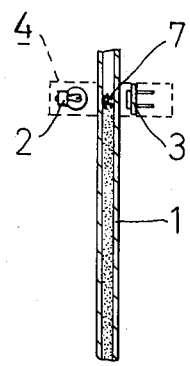
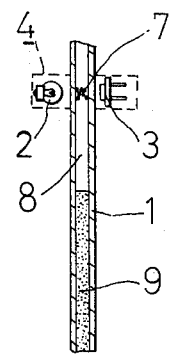
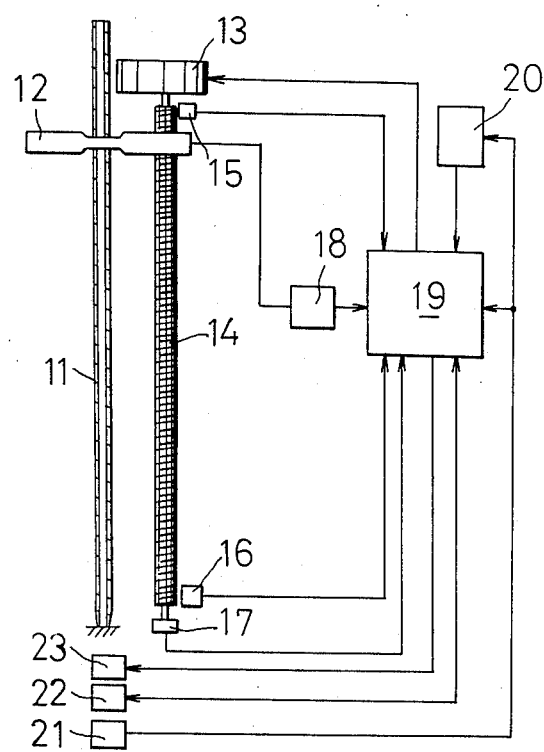

METHOD AND APPARATUS FOR MEASURING ERYTHROCYTE SEDIMENTATION RATE

BACKGROUND OF THE INVENTION

This invention relates to a method and apparatus for measuring erythrocyte sedimentation rate.

The measurement of erythrocyte sedimentation or the amount of the sedimented red blood corpuscles is generally performed by pouring a blood sample consisting of a mixture of the blood and a coagulation inhibition agent into a graduated test tube, holding the tube in a vertical position for a predetermined interval, for example one or two hours, and observing the amount of the sedimented red blood corpuscles, at an interval of one hour, as shown in FIG. 1. To automatically measure the blood sedimentation rate the tube 1 filled with the blood sample is held in the vertical position, and a photoelectric detection unit 4 (see FIG. 3) including a source of light 2 on one side at the tube 1 and photoelectric transducer 3 positioned on the other side for receiving the light transmitting through the tube is moved from the upper end to the lower end of the tube 1 by means of a feed screw 6 operated by an electric motor 5 as shown in FIG. 2. With this method, the upper level of the sample before erythrocyte sedimentation is optically detected by the photoelectric detection unit 4. The unit 4 is stopped at this position and this position is memorized by a suitable memory device. After a predetermined interval the photoelectric detection unit 4 is lowered to optically detect the interface between the blood serum and the sedimented red blood corpuscles by using the difference in the light transmissibility thus determining the upper level of the sedimented red blood corpuscles. The sedimentation rate is determined by the difference between the stored level of the sample before sedimentation and the upper level of the sedimented red blood corpuscles.

The pouring of the blood sample into the narrow test tube 1 is done by a suction type injector or the like, so that an air bubble 7 would be formed in the upper portion of the tube 1 on the sample. In certain cases coagulated substance may deposite on the upper surface of the sample. For this reason, in the case of the automatic measurement, where an air bubble or the coagulated substance is present on the upper surface of the sample contained in the tube 1 the light transmittance would be reduced by the air bubble and/or the coagulated substance, so that the photoelectric detection unit 4 will be stopped at that position.

After one hour, for example, even though the blood serum 8 has been separated from the red blood corpuscles 9 due to sedimentation, the photoelectric detection unit does not move from the position of the air bubble or the coagulated substance because the photoelectric detection unit detects the light reduced by the air bubbles and/or the coagulate substance. As the result, the rate of blood sedimentation would be erroneously measured as Zero.

SUMMARY OF THE INVENTION

Accordingly, it is an object of this invention to provide an improved method and apparatus for measuring the erythrocyte sedimentation rate which can eliminate the disadvantage described above.

Another object of this invention is to provide an improved apparatus for measuring the erythrocyte sedimentation rate which is simple in construction, easy to handle and yet can accurately determine the erythrocyte sedimentation rate.

According to this invention there is provided a method of measuring a blood sedimentation rate of the type wherein the upper level of a blood sample contained in a vertical test tube is detected by a photoelectric detection unit, the red blood corpuscles in the blood sample are caused to sedimentate for a predetermined interval and the upper level of the sedimentated red blood corpuscles is detected by descending the photoelectric detection unit along the test tube thereby detecting the rate of sedimentation of red blood corpuscles, characterized by the steps of stopping the photoelectric detection unit at a definite time after detection of the upper level of the blood sample, descending the photoelectric detection unit after said predetermined interval, detecting the interface of the blood serum and the sedimented red blood corpuscles, and measuring the rate of sedimentation of the red blood corpuscles in terms of the difference between the position at which the photoelectric detection unit has stopped and the position of the photoelectric detection unit a predetermined time after detection of the interface.

According to another aspect of this invention there is provided apparatus for measuring erythrocyte sedimentation rate comprising a vertical test tube adapted to contain a blood sample, a photoelectric detection unit including a light source positioned one side of the test tube, and a photoelectric transducer positioned on the other side of the test tube for receiving light transmitting through the test tube, an electric motor for moving the photoelectric detection unit along the test tube, a delay circuit connected to said photoelectric detection unit, a time counter for providing a time during which red blood corpuscles in the blood sample sedimentate, said time counter producing a signal when said time counter has counted the time, a control unit connected to said delay circuit, said time counter and said motor for controling said motor so that said control unit stops said motor when said delay circuit produces a signal which is caused by the detection of the surface of the blood sample by said photoelectric detection unit and moves said motor when said time counter produces the signal; and means for measuring the amount of the movement of said photoelectric detection unit from a position where said photoelectric detection unit is stopped by the signal from said delay circuit to another position of said photoelectric unit indicating the interface between the blood serum and the sedimented red blood corpuscles.

BRIEF DESCRIPTION OF THE DRAWINGS

Further objects and advantages of the invention can be more fully understood from the following detailed description taken in conjection with the accompanying drawings in which:

FIG. 4 is a side view showing an air bubble formed on the blood sample contained in a test tube;

FIG. 5 is a side view showing the manner of stopping the photoelectric detection unit due to the air bubble formed on the upper surface of the blood sample in the test tube;

FIG. 6 is a block diagram showing one embodiment of this invention; and

DESCRIPTION OF THE PREFERRED EMBODIMENT

Figure 1:
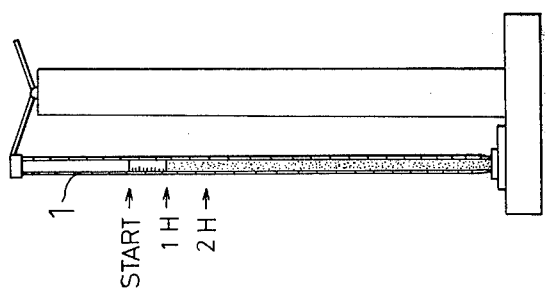
FIG. 1 is a schematic representation of a prior art apparatus for measuring erythrocyte sedimentation rate by naked eyes.
Figure 2:
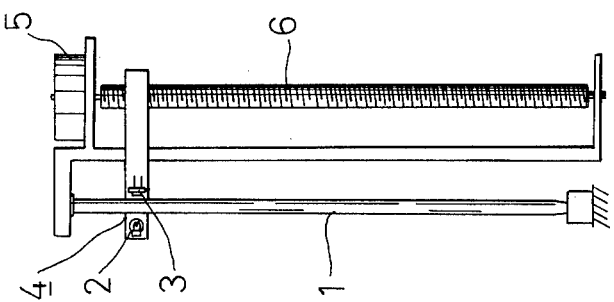
FIG. 2 is a schematic representation of a prior art automatic apparatus for measuring erythrocyte sedimentation rate.
Figure 3:
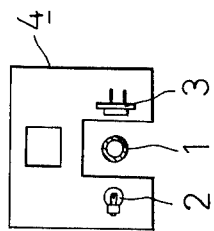
FIG. 3 is a plan view showing a photoelectric detection unit utilized in the apparatus shown in FIG. 2.

The apparatus for measuring a sedimentation rate embodying the invention and shown in FIG. 6 comprised a fine test tube 11, a photoelectric detection unit 12, and a feed screw 14 operated by an electric motor 13 for moving the photoelectric detection unit 12 along the test tube 11, which are arranged in the same manner as the corresponding elements shown in FIG. 2. There are also provided a upper limit switch 15, a lower limit switch 16, a rotation detector 17 for detecting the number of revolutions of the feed screw 14, a delay circuit 18 for delaying an electric signal produced by the photoelectric detection unit 12 by a predetermined time, and a control unit 19 which is connected to process the signals from the delay circuit 18, the upper and lower limit switches 15 and 16, rotation detector 17 and a timing pulse generator 20.

Upon depression of a push button 21, the motor 13 is caused to rotate by a signal from the control unit and at the same time, timing pulses generated by the timing pulse generator 20. The number of pulses is counted by a counter 22. A counter 23 for displaying the amount of sedimentation rate is connected to the control unit 19 for counting the number of revolutions of the rotation detector after the signal from the delay circuit has been applied to the control unit 19. Upon receiving the forward rotation signal, the motor 13 rotates in the forward direction to lower the photoelectric detection unit 12 through the feed screw 14. The upper level of the sample in the test tube 11 before the sedimentation of the red blood corpuscles is optically detected by the photoelectric detection unit 12 and its output is supplied to the control unit 19 after being delayed a predetermined time by the delay circuit 18. At this time, a stop signal is supplied to the motor 13 from the control unit 19 for stopping the motor. At a consequence, the photoelectric detection unit 12 is stopped at a position slightly below the level of the sample before sedimentation of the red blood corpuscles. This point is termed the first measuring point. The delay time provided by the delay circuit 18 is determined in proportion to the descending speed of the photoelectric detection unit 12 such that the distance between the level of the surface of the sample and the first measuring point will be slightly larger than the size of the air bubble and/or coagulate substance formed on the sample, the size of the air bubble being generally smaller than 2 mm.

As described above, when the start button 21 is operated, the pulse counter 22 begins to count the number of pulses. When the count of the counter reaches a predetermined count (the counter is designed to produce a signal when the counter has counted a predetermined time, for example one or two hours), a signal is supplied to the control unit 19. In response to this signal, the control unit 19 supplies a drive signal to the motor 13. As a consequence, the photoelectric detection unit 12 is moved again in the downward direction through the feed screw 14. At this time the number of revolutions of the feed screw 14 is detected by the rotation detector to display the rate of sedimentation by the display counter 23. The interface between the red blood corpuscles and the serum of the sample in the test tube is optically detected by the photoelectric detection unit 12 based on the difference in the transmissibility and the output of the detection unit 12 is applied to the control unit 19 after being delayed by the delay circuit 18. The position of the photoelectric detection unit 12 at this time is termed the second measuring time. In order to compensate a minute error caused by the air bubbles and/or coagulate substance, it is preferable that the displayed number is subtracted with a predetermined number which is empirically determined, or another time delay circuit is used to provide a different time delay for the detection signal of the interface between the serum and the red blood corpuscles. When the photoelectric detection unit 12 detected the interface, the detection signal from the detection unit 12 drives the control unit 19 through the delay circuit 18 to stop the delay counter 18. The displayed number in the display represents sedimentation rate with substantially accurateness for practical use although this displayed number includes the amount of the movement of the photoelectric detection unit along a portion of the test tube in which air bubbles and/or coagulate substance occupy.

At this time, since counter 22 supplies a signal corresponding to its predetermined count to the control unit 19, the operation of the motor 13 will be continued even when the signal from the delay circuit 18 is applied to the control unit 19. However, it is possible to stop the operation of the motor when the signal from the delay circuit is applied to the control unit. When the photoelectric detection unit 12 reaches the lowermost position, its position is detected by the lower limit switch 16 so that a reverse driving signal is supplied to the motor through the control unit 19, thus raising the photoelectric detection unit 12. When the unit reaches the uppermost position, the upper limit switch 15 sends a stop signal to the motor 13 through the control signal 13 so as to stop the rotation of the motor at this time measurement of blood sedimentation rate is completed.

Figure 7:
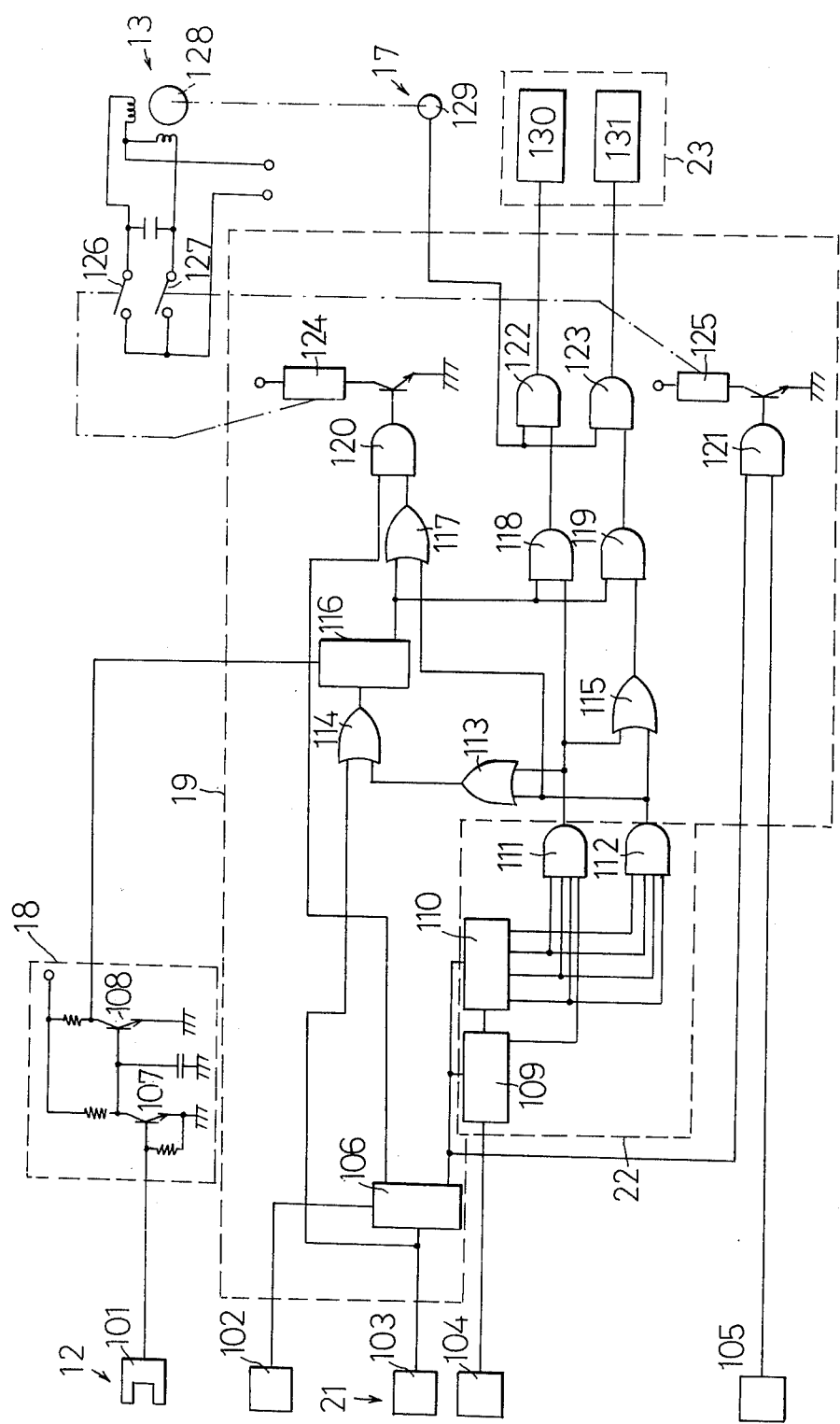
FIG. 7 is a schematic diagram of a control circuit being used in the device shown in FIG. 6.

FIG. 7 shows an embodiment of a control circuit being used in the devices shown in FIG. 6. In FIG. 7, each section shown in the form of block in FIG. 6 is shown by a dotted line and a same reference mark is given theres. When a starting switch 102 is turned on, both of two inputs of the AND-gate 120 will become high-level. That is to say, one input is supplied through the flip-flop 106, the other is supplied through the OR-gate 114, flip-flop 116, OR-gate 117. Accordingly, the output of the AND-gate 120 will become high-level, drive the electromagnetic relay 124, close the switch 126, rotate the motor 128 and move the photoelectric detection unit 12 downwardly.

When the starting switch is turned on, the time pulse generator 104 starts its operation simultaneously, at the same time, the counters 109 and 110 are set to operational condition by the flip-flop 106. Accordingly, when the starting switch is turned on, the counters 109, 110 start to count time pulses simultaneously. When the photoelectric detection unit 101 detects the surface of a sample, its signal will be sent to the delay circuit 18. The delay-time of the delay circuit is given by the capacitor 107. After the delay time has been given by the capacitor 107, the detection signal is given to the flip-flop 116 to cause it to reverse. As the result of this, the input of one side of the AND-gate 120 will become low-level, so the relay 124 will become erased and the motor 124 will stop. That is to say, after the upper surface of the sample has been detected, the photoelectric detection unit will stop its decent after a fixed time has passed.

Gates are so designed that the gate 111 will open when the counter 109 has counted pulses for a time corresponding to one hour and the gate 112 will open when the counter 110 has counted pulses for a time corresponding to two hours. When one hour has passed after starting counting, the gate 111 will open and reverse the flip-flop through the AND-gates 113, 114.

By the reversion of the flip-flop 116, the motor 128 rotates again and the photoelectric detection unit 101 descends. The rotation detector 129 (17 in FIG. 6) is a pulse generator which is driven by a cam provided on the rotation shaft of the screw 14 and produces pulses. By the operation of the gate 111, the inputs of one side of the AND-gates 118, 119 become high-level and, as described hereinbefore, by the reversion of the flip-flop 116, the inputs of the other side of the AND-gates 118 and 119 also become high-level, so the gates 122 and 123 will open. That is to say, when the photoelectric detection unit 12 descends after it has detected the upper surface of the sample, the display counters 130 and 131 will start their operation. When the photoelectric detection unit detects the interface of the serum and the deposited red blood corpuscles, the flip-flop 116 reverses in the same manner as described above and the photoelectric detection unit 12 stops its descent. At this time, the AND-gates 118, 119 also close simultaneously, so the display counters 130, 131 stop their operation. That is to say, the volume of precipitation of blood is display on the display counters 130 and 131.

Next, after the lapse of two hours, the gate 112 opens and the photoelectric detection unit 12 descends again in the same manner as described above. At this time, the input of one side of the AND-gate 118, i.e. the input from the flip-flop 116 is high-level, but the input of the other side (from the gate 111) is in a low-level condition, so the display counter 130 will not operate. However, the input from the gate 112 of the AND-gate 119 is in a high-level condition, so the display counter will operate. When the photoelectric detection unit 101 restarts the detection of the interface of the serum and the red blood corpuscles of the sample, the flip-flop 116 will reverse in the same manner as described above. At this time, signals from the gate 112 enter the OR-gate 117, so the motor will not stop even by the reversion of the flip-flop 116 and the photoelectric detection unit 101 will continue to descend. On the one hand, by the reversion of the flip-flop 116, the AND-gate 119 will close, the display counter 131 will stop its operation and the volume of precipitation of blood will be displayed after two hours. As described above, even after the measurement of the volume of precipitation of blood conducted after two hours, the photoelectric detection unit still continues to descend, but the photoelectric detection unit 12 reaches the lower limit and when it acts upon the switch 102, the flip-flop 106 reverses. By the reversion of the flip-flop 106, the AND-gate 120 closes, when the switch 126 opens, the AND-gate 121 opens simultaneously, the relay 125 operates to cause the switch 127 to close, the motor 128 reverses, the photoelectric detection unit 12 ascends. When the photoelectric detection unit 12 reaches the upper limit it acts upon the upper limit switch 105, the AND-gate 121 closes, the motor 128 stops, the circuit returns to its original state.

According to this invention, the upper level of the blood sample contained in the test tube is detected by the photoelectric detection unit and the unit is stopped at a position several mm below the upper level so that though an air bubble or coagulated matter is present on the sample, the amount of the transmitted light would not be decreased due to refraction caused by the bubbles or the coagulated matter. Accordingly, the missoperation described can be prevented. After a predetermined interval, that is when the red blood corpuscles have sedimentated the photoelectric detection unit is lowered to detect the interface between the blood serum and the red blood corpuscles.

What is claimed is:

1. In a method of measuring a erythrocyte sedimentation rate of the type wherein the upper level of a blood sample contained in a vertical test tube is detected by a photoelectric detection unit, the red blood corpuscles in the blood sample are caused to sedimentate for a predetermined interval, and the upper level of the sedimentated red blood corpuscles is detected by descending said photoelectric detection unit along said test tube thereby determining the rate of the sedimentation of the red blood corpuscles, the improvement which comprises the steps of stopping said photoelectric detection unit a definite time after detection of the upper level of said blood sample, descending said photoelectric detection unit after said predetermined interval, detecting the interface between the blood serum and the sedimentated red blood corpuscles, measuring the rate of the sedimentation of the red blood corpuscles in terms of the difference between the position at which said photoelectric detection unit has stopped and the position of said photoelectric indicating detection of said interface.

2. The method of measuring an erythrocyte sedimentation rate, as set forth in claim 1, wherein initially said photoelectric detection unit is lowered from above to detect the upper level of said blood sample and at said definite time after detection of the upper level of said blood sample is stopped at a position slightly below the upper level of said blood sample, out of an interfering range of air bubbles and coagulate substances, respectively.

3. Apparatus for measuring erythrocyte sedimentation rate comprising a vertical test tube adapted to contain a blood sample, a photoelectric detection unit including a light source positioned one side of the test tube, a photoelectric transducer positioned on the other side of the test tube for receiving light transmitting trough the test tube, an electric motor for moving the photoelectric detection unit along the test tube, a delay circuit connected to said photoelectric detection unit, a time counter for providing a time during which red blood corpuscles in the blood sample sedimentate, said time counter producing a signal when said time counter has counted the time a control unit connected to said delay circuit, said time counter and said motor for controling said motor so that said control unit stops said motor when said delay circuit produces a signal which is caused by the detection of the surface of the blood sample by said photoelectric detection unit and moves said motor when said time counter produces the signal; and means for measuring the amount of the movement of said photoelectric detection unit from a position where said photoelectric detection unit is stopped by the signal from said delay circuit to another position of said photoelectric unit indicating the interface between the blood serum and the sedimentated red blood corpuscles.

4. The apparatus according to claim 3 which further said measuring means comprises means responsive to the number of revolutions of said motor and counter means, said responsive means being connected to said control unit so that said responsive means drives said counter means through said control unit.

5. The apparatus according to claim 3 which further comprises limit switches for reversing the direction of rotation of said motor when said photoelectric detection unit reaches its upper and lower limits of movement.

6. The apparatus according to claim 3 wherein said means for descending said photoelectric detection unit comprises a counter which counts said timing pulse, and said counter controls said control unit to energize said motor by said timing pulse when predetermined count is reached.

* * * * *